US012089925B2

(12) United States Patent
Lobner et al.

(10) Patent No.: US 12,089,925 B2
(45) Date of Patent: Sep. 17, 2024

(54) IMPAIRMENT DETECTION

(71) Applicant: ATTENTI ELECTRONIC MONITORING LTD., Tel Aviv (IL)

(72) Inventors: Eric C. Lobner, Woodbury, MN (US); James W. Howard, Circle Pines, MN (US); Jennifer F. Schumacher, Woodbury, MN (US); Brian J. Stankiewicz, Mahtomedi, MN (US); Billy L. Weaver, Eagan, MN (US)

(73) Assignee: ATTENTI ELECTRONIC MONITORING LTD., Tel-Aviv (IL)

( * ) Notice: Subject to any disclaimer, the term of this patent is extended or adjusted under 35 U.S.C. 154(b) by 127 days.

(21) Appl. No.: 15/511,310

(22) PCT Filed: Sep. 15, 2015

(86) PCT No.: PCT/US2015/050071
§ 371 (c)(1),
(2) Date: Mar. 15, 2017

(87) PCT Pub. No.: WO2016/044197
PCT Pub. Date: Mar. 24, 2016

(65) Prior Publication Data
US 2017/0245785 A1  Aug. 31, 2017

Related U.S. Application Data

(60) Provisional application No. 62/050,361, filed on Sep. 15, 2014.

(51) Int. Cl.
A61B 5/16     (2006.01)
A61B 5/00     (2006.01)
A61B 5/11     (2006.01)
G08B 21/02    (2006.01)
G16H 40/63    (2018.01)
G16H 50/20    (2018.01)
G08B 5/00     (2006.01)

(52) U.S. Cl.
CPC ............. *A61B 5/1123* (2013.01); *A61B 5/11* (2013.01); *A61B 5/1112* (2013.01); *A61B 5/16* (2013.01);
(Continued)

(58) Field of Classification Search
CPC ....... A61B 5/1123; A61B 5/11; A61B 5/1112; A61B 5/16; A61B 5/4023; A61B 5/6803;
(Continued)

(56) References Cited

U.S. PATENT DOCUMENTS 5,137,345 A   8/1992  Waldorf
5,295,491 A   3/1994  Gevins
(Continued)

FOREIGN PATENT DOCUMENTS

EP   1642248   4/2006
EP   2319410   5/2011
(Continued)

OTHER PUBLICATIONS

US 7,877,241 B2, 01/2011, Elmer (withdrawn)
(Continued)

*Primary Examiner* — Daniel L Cerioni
(74) *Attorney, Agent, or Firm* — SOROKER AGMON NORDMAN RIBA

(57) ABSTRACT

A method for monitoring impairment indicators, the method includes measuring, with a movement sensor attached to the person, a first signal related to movement of a person during a first time window and electronically storing the at least one numerical descriptor derived from the first signal as reference data for the person. The method further includes measuring, with the movement sensor attached to the person, a second signal related to movement of the person during a second time window and comparing at least one numerical descriptor derived from the second signal to the
(Continued)

reference data as a factor to identify an impairment indicator. The present disclosure also includes a device for monitoring impairment indicators.

15 Claims, 5 Drawing Sheets

(52) U.S. Cl.
 CPC ......... *A61B 5/4023* (2013.01); *A61B 5/6803* (2013.01); *A61B 5/6805* (2013.01); *A61B 5/6828* (2013.01); *A61B 5/7246* (2013.01); *A61B 5/7275* (2013.01); *A61B 5/7282* (2013.01); *A61B 5/746* (2013.01); *G08B 21/02* (2013.01); *G16H 40/63* (2018.01); *G16H 50/20* (2018.01); *A61B 5/0002* (2013.01); *A61B 5/4088* (2013.01); *A61B 5/6829* (2013.01); *A61B 2503/20* (2013.01); *A61B 2562/0219* (2013.01); *G08B 5/004* (2013.01)

(58) Field of Classification Search
 CPC ... A61B 5/6805; A61B 5/6828; A61B 5/7246; A61B 5/7275; A61B 5/7282; A61B 5/746; G08B 21/02
 USPC .......................................................... 600/595
 See application file for complete search history.

(56) References Cited

U.S. PATENT DOCUMENTS

| | | | |
|---|---|---|---|
| 5,325,862 A | 7/1994 | Lewis | |
| 5,354,120 A | 10/1994 | Volkle | |
| 5,421,344 A | 6/1995 | Popp | |
| 5,447,166 A | 9/1995 | Gevins | |
| 5,485,402 A | 1/1996 | Smith | |
| 5,724,987 A | 3/1998 | Gevins | |
| 6,032,530 A | 3/2000 | Hock | |
| 6,511,443 B2 | 1/2003 | Cuce | |
| 6,853,304 B2 | 2/2005 | Reisman | |
| 7,394,392 B1* | 7/2008 | Roe | B60K 28/06 180/272 |
| 7,421,369 B2 | 9/2008 | Clarkson | |
| 7,451,056 B2 | 11/2008 | Flentov | |
| 7,512,515 B2 | 3/2009 | Vock | |
| 7,653,508 B1 | 1/2010 | Kahn | |
| 7,750,815 B2 | 7/2010 | Burris | |
| 7,818,131 B2 | 10/2010 | Mott | |
| 7,881,902 B1 | 2/2011 | Kahn | |
| 8,036,851 B2 | 10/2011 | Vock | |
| 8,078,334 B2 | 12/2011 | Goodrich | |
| 8,187,209 B1 | 5/2012 | Giuffrida | |
| 8,226,574 B2 | 7/2012 | Whillock | |
| 9,707,845 B1* | 7/2017 | Nienhouse | B60K 28/063 |
| 9,807,725 B1* | 10/2017 | Vitus | H04W 4/02 |
| 9,808,206 B1* | 11/2017 | Zhao | G16H 20/30 |
| 2002/0052541 A1 | 5/2002 | Cuce | |
| 2003/0208335 A1 | 11/2003 | Unuma | |
| 2005/0027216 A1 | 2/2005 | Guillemaud | |
| 2006/0235642 A1 | 10/2006 | Vock | |
| 2006/0284979 A1 | 12/2006 | Clarkson | |
| 2007/0010720 A1 | 1/2007 | Mott | |
| 2007/0022074 A1* | 1/2007 | Muramatsu | A61B 5/16 706/50 |
| 2007/0112287 A1 | 5/2007 | Fancourt | |
| 2007/0124135 A1 | 5/2007 | Schultz | |
| 2007/0173705 A1* | 7/2007 | Teller | A61B 5/02055 600/300 |
| 2007/0173727 A1 | 7/2007 | Naghavi | |
| 2007/0208530 A1 | 9/2007 | Vock | |
| 2007/0225614 A1 | 9/2007 | Naghavi | |
| 2007/0265816 A1 | 11/2007 | Elmer | |
| 2008/0183388 A1 | 7/2008 | Goodrich | |
| 2009/0069722 A1 | 3/2009 | Flaction | |
| 2009/0150114 A1 | 6/2009 | Vock | |
| 2009/0176257 A1* | 7/2009 | Bahn | B82Y 15/00 435/7.92 |
| 2009/0212957 A1 | 8/2009 | Burris | |
| 2009/0240462 A1 | 9/2009 | Lee | |
| 2009/0240463 A1 | 9/2009 | Lee | |
| 2009/0293615 A1 | 12/2009 | Lee | |
| 2009/0316983 A1 | 12/2009 | Han | |
| 2010/0016754 A1 | 1/2010 | Whillock | |
| 2010/0075619 A1* | 3/2010 | Solla | A42B 3/30 455/90.3 |
| 2010/0161706 A1 | 6/2010 | Kim | |
| 2010/0191155 A1 | 7/2010 | Kim | |
| 2010/0231402 A1* | 9/2010 | Flynt | A62B 35/0025 340/679 |
| 2011/0029250 A1 | 2/2011 | Mott | |
| 2011/0029465 A1 | 2/2011 | Ito | |
| 2011/0077919 A1 | 3/2011 | Lee | |
| 2011/0213276 A1 | 9/2011 | Sarussi | |
| 2012/0004883 A1 | 1/2012 | Vock | |
| 2012/0048013 A1* | 3/2012 | Minami | A61B 5/11 73/379.02 |
| 2012/0259578 A1 | 10/2012 | Bevilacqua | |
| 2012/0316406 A1 | 12/2012 | Rahman | |
| 2013/0006583 A1* | 1/2013 | Weast | A61B 5/112 702/189 |
| 2014/0088378 A1 | 3/2014 | Muzet | |
| 2014/0195538 A1* | 7/2014 | Downs | A61B 5/1123 707/737 |
| 2014/0280645 A1* | 9/2014 | Shuman | H04W 12/068 709/206 |
| 2014/0335490 A1* | 11/2014 | Baarman | A61B 5/1118 434/236 |
| 2015/0257681 A1* | 9/2015 | Shuster | A61B 5/18 600/595 |
| 2016/0015289 A1* | 1/2016 | Simon | A61B 5/6826 600/301 |
| 2016/0113559 A1* | 4/2016 | Lynch | A61B 5/0004 600/301 |
| 2016/0278706 A1* | 9/2016 | Okamoto | A61B 5/0013 |

FOREIGN PATENT DOCUMENTS

| | | |
|---|---|---|
| GB | 2447647 | 9/2008 |
| IN | 2389/CHE/2009 | 4/2011 |
| JP | 04250141 | 9/1992 |
| JP | 2009023545 | 2/2009 |
| KR | 2005-0086556 | 8/2005 |
| KR | 20100073802 | 7/2010 |
| KR | 20100087551 | 8/2010 |
| KR | 2010-0115688 | 10/2010 |
| KR | 20110034828 | 4/2011 |
| KR | 2013-0140866 | 12/2013 |
| RU | 2146494 | 3/2000 |
| WO | WO 1993-07809 | 4/1993 |
| WO | WO 1995-18565 | 7/1995 |
| WO | WO 2005-118516 | 12/2005 |
| WO | WO 2007-107491 | 9/2007 |
| WO | WO 2008-091621 | 7/2008 |
| WO | WO 2009-090584 | 7/2009 |
| WO | WO 2009-117687 | 9/2009 |
| WO | WO 2009-117703 | 9/2009 |
| WO | WO 2009-151711 | 12/2009 |
| WO | WO 2013-136251 | 9/2013 |
| WO | WO 2014-083490 | 6/2014 |

OTHER PUBLICATIONS

Dai, "Mobile Phone Based Drunk Driving Detection", Pervasive Computing Technologies for Healthcare, 2010, pp. 1-8.
Grolsch, "Walk the Line IPhone App", [retrieved from the internet on May 15, 2017], URL <http://www.youtube.com/watch?v=YMagZK__Yoo>, pp. 1-2.
Intelligent Fingerprinting, "Rapid, non-invasive drug screening at the touch of a fingertip", [retrieved from the internet on May 15, 2017], URL <http://www.intelligentfingerprinting.com/>, p. 1.

(56) References Cited

OTHER PUBLICATIONS

National Highway Traffic Safety Administration, "Assessing the Feasibility of Vehicle-Based Sensors to Detect Alcohol Impairment", U.S. Department of Transportation, 2010, pp. 1-98.

National Institutes of Health, "Remote Monitoring System for Detecting Cocaine Ingestion/Intoxication (R01)", Department of Health and Human Services, 2011, pp. 1-14.

Rassnick, "Responding to acoustic startle during chronic ethanol intoxication and withdrawal", Psychopharmacology, 1992, vol. 106, No. 03, pp. 351-358.

Simmersion, "Training People for Important Conversations", [retrieved from the internet on May 15, 2017], URL <http://www.alcoholmonitoring.com/index/clients/overview>. pp. 1-4.

Verstraete, "Detection Times of Drugs of Abuse in Blood, Urine, and Oral Fluid", Basel Proceedings, 2004, vol. 26, No. 02, pp. 200-205.

International Search Report for PCT International Application No. PCT/US2015/050071, mailed on Dec. 18, 2015, 7 pages.

\* cited by examiner

IMPAIRMENT DETECTION

TECHNICAL FIELD

The present invention relates to the field of recognizing or classifying movement, and more specifically, to identifying impairment indicators using data from a movement sensor associated with a person.

BACKGROUND

Detection of cognitive, physical, mental, sensory, emotional, or developmental impairment is critically important in healthcare, law enforcement, or other applications. Detection techniques may be specific to an individual impairment (such as physical) or any combination of impairments (such as cognitive and sensory). For example, detecting alcohol or controlled substance use or abuse by workers, individuals on parole, or in other contexts is important for safety and compliance with various restrictions. Detecting physical impairment, such as an injury, is important for workers who require full physical capabilities to perform their duties. Mental impairment detection is important in potentially diagnosing patients with the early onset of mind debilitating conditions such as dementia and/or Alzheimer's disease. Detecting other impairments such as tiredness, distraction, and vestibular confusion play an important role for safety and compliance purposes. Improved methods for effectively monitoring for the presence of impairment without being invasive would be welcome.

SUMMARY

The present disclosure provides a new method of detecting impairment indicators. The present invention provides for non-intrusive continuous detection of impairment indicators. Upon detection of an impairment indicator, a person may be required to perform further testing activities, thus reducing the overall need for and cost of types of impairment testing such as drug or alcohol screening. Impairment detection is also useful to proactively identify and mitigate potential safety situations. Identification and notification when an individual is impaired may reduce the amount of injuries or accidents that could occur otherwise. Additionally, using impairment detection for identifying diseases may lead to more effective treatment.

In one aspect, the present disclosure includes a method for monitoring impairment indicators. The method includes measuring, with a movement sensor associated with the person, a first signal related to movement of a person during a first time window and electronically storing at least one numerical descriptor derived from the first signal as reference data for the person. The method further includes measuring, with the movement sensor attached to the person, a second signal related to movement of the person during a second time window and comparing at least one numerical descriptor derived from the second signal to the reference data as a factor to identify an impairment indicator.

In some embodiments, the first time window occurs during a training activity performed by the person.

In some embodiments, the method further comprises collecting location information and using the location information as a second factor to identify an impairment indicator.

In some embodiments, the impairment indicator is indicative of at least one of mental impairment, visual impairment and physical impairment.

In some embodiments, mental impairment includes at least distraction.

In some embodiments, visual impairment includes at least prohibited substance abuse.

In some embodiments, physical impairment includes at least physical injury and vestibular confusion.

In some embodiments, the movement sensor is at least one of: an accelerometer, a gyroscope, a piezoelectric vibration sensor, a geographical positioning sensor and a magnetic switch.

In some embodiments, the movement of the person during the first time window is walking.

In some embodiments, when an impairment indicator is detected, at least one of a local alarm and a remote alarm is triggered.

In a second configuration, the present disclosure includes a device for monitoring impairment indicators. The device includes a housing configured to be associated with a person and a processing unit disposed in the housing comprising a processor and a movement sensor. The movement sensor measures a first signal related to movement of the person during a first time window, and the processor stores at least one numerical descriptor derived from the first signal with the activity label as reference data for the person. The movement sensor then measures a second signal related to movement of the person during a second time window, and the processor compares at least one numerical descriptor derived from the second signal to the reference data as a factor to identify an impairment indicator.

In some embodiments, the housing is one of: a safety garment, a harness, a head-worn piece, a device to be attached to a limb of the person or a device used by the person.

In some embodiments, the processor is configured to estimate a location of the person using at least both of a signal from the movement sensor and data from the location module.

In some embodiments, the device further uses the location of the person as a second factor to identify an impairment indicator.

In some embodiments, the impairment indicator is indicative of at least one of mental impairment, visual impairment and physical impairment.

In some embodiments, the movement sensor is at least one of: an accelerometer, a gyroscope, a piezoelectric vibration sensor, a geographical positioning sensor and a magnetic switch.

In some embodiments, the device comprises more than one movement sensor.

In some embodiments, the movement of the person during the first time window is walking.

In some embodiments, when an impairment indicator is detected, at least one of a local alarm and a remote alarm is triggered.

BRIEF DESCRIPTION OF DRAWINGS

The following figures provide illustrations of the present invention. They are intended to further describe and clarify the invention, but not to limit scope of the invention.

Like numbers are generally used to refer to like components. The drawings are not to scale and are for illustrative purposes only.

DETAILED DESCRIPTION

Figure 1:
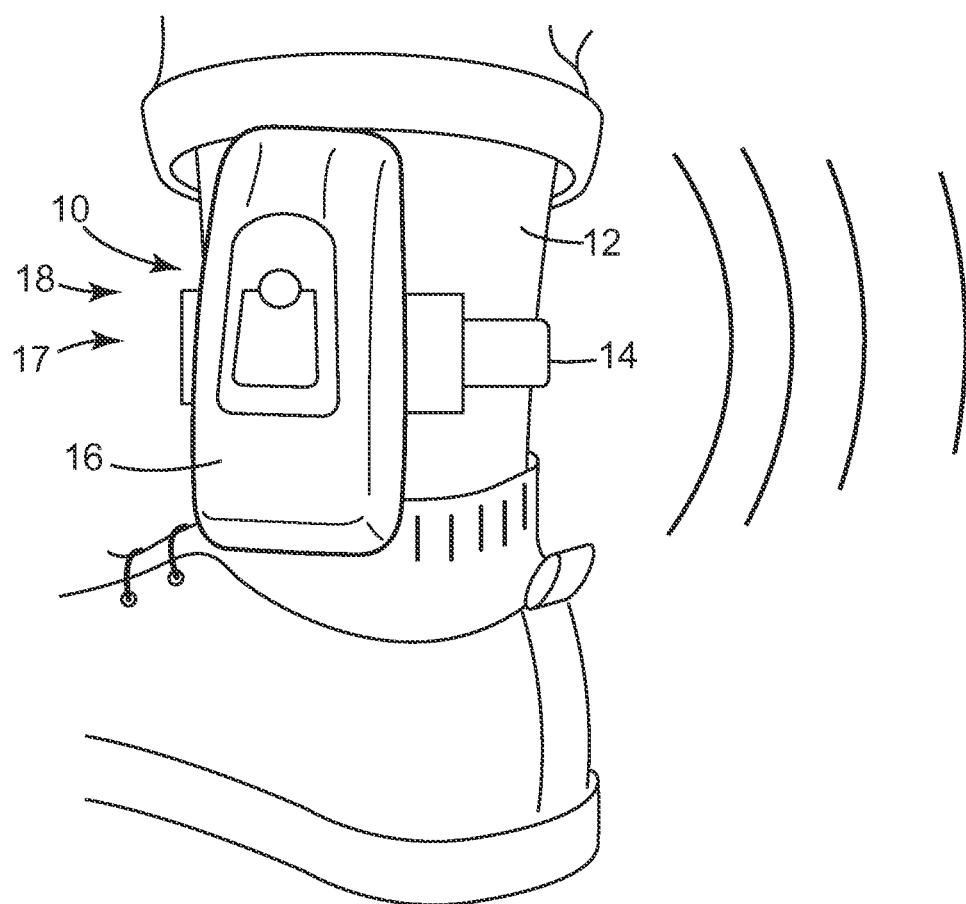
FIG. 1 is an example of a device for monitoring impairment indicators attached to a person.

FIG. 1 is an example of a device 10 for monitoring impairment indicators attached to a person's ankle 12. Device 10 is attached to person's ankle 12 or other limb with strap 14. The housing 16 for device 10 includes or contains a variety of components such as a processing unit 17, including both a processor and a movement sensor, and a communication unit 18 for communicating wirelessly with an external device. A processor in the processing unit 17 may also include memory for storing data received from the movement sensor, numerical descriptors, reference data, and other information necessary to identify impairment indicators. The movement sensor may include at least one of a variety of sensors, including an accelerometer, gyroscope, piezoelectric vibration sensor, geographical positioning sensor and a magnetic switch.

A movement sensor may be configured to measure a signal related to movement of the person during a first time window. The movement sensor may collect data at a variety of rates, for example, the rate may be in the range of one (1) Hz to sixty (60) Hz. The rate may be, for example, 5 Hz, 10 Hz, 20 Hz, 30 Hz, 40 Hz, 50 Hz or 60 Hz or more. The length of the time window may be any desired range. For example, a time window may be in the range of two (2) seconds to ten (10) seconds. A time window may be, for example, 2 seconds, 5 seconds, 6 seconds, 10 seconds, or more or less. The number of samples taken by a movement sensor in the device varies based on the length of the time window and the sampling rate. The number of samples may range, for example, from 8 to 1024 samples. A processor may then electronically store at least one numerical descriptor derived from the first signal as reference data for the person. The numerical descriptor may be represented as a scalar such as a voltage, current, power, or energy measurement. The movement sensor may then measure a second signal related to movement of the person during a second time window. The processor may then compare at least one numerical descriptor derived from the second signal to the reference data as a factor to identify an impairment indicator.

In one configuration, the first time window occurs during a training activity performed by the person. In some embodiments training activity may include, but is not limited to, a person completing a series of prescribed or predetermined movements to establish baseline performance data. In another configuration, the first time window is during normal use of the device 10 by the person.

Device 10 may also include other components such as a location unit that enables the device to receive satellite signals and determine location using, for example, GPS or the Global Navigation Satellite System (GLONASS) as discussed in U.S. Pat. No. 6,853,304 to Reisman et al., incorporated herein by reference. A location unit may use other location technologies such as triangulation using local WiFi signals or other known location technologies to estimate location of the activity recognition device 10, and thereby the location of the person wearing the device.

While device 10 is shown as having a housing of a device to be attached to a limb of the person, the housing may be a variety of embodiments. For example, the housing may also be a safety garment, safety equipment, a harness, a head-worn piece, and article of clothing or incorporated into a handheld or portable device to be used by the person such as a mobile phone.

While the housing for device 10 shows the movement sensor, processor and other device components being located in close proximity to each other, in other housing configurations, the movement sensor, or multiple movement sensors, may be located in multiple locations in the housing, and located at a distance from other components, such as the processor and communication unit.

Figure 2A:
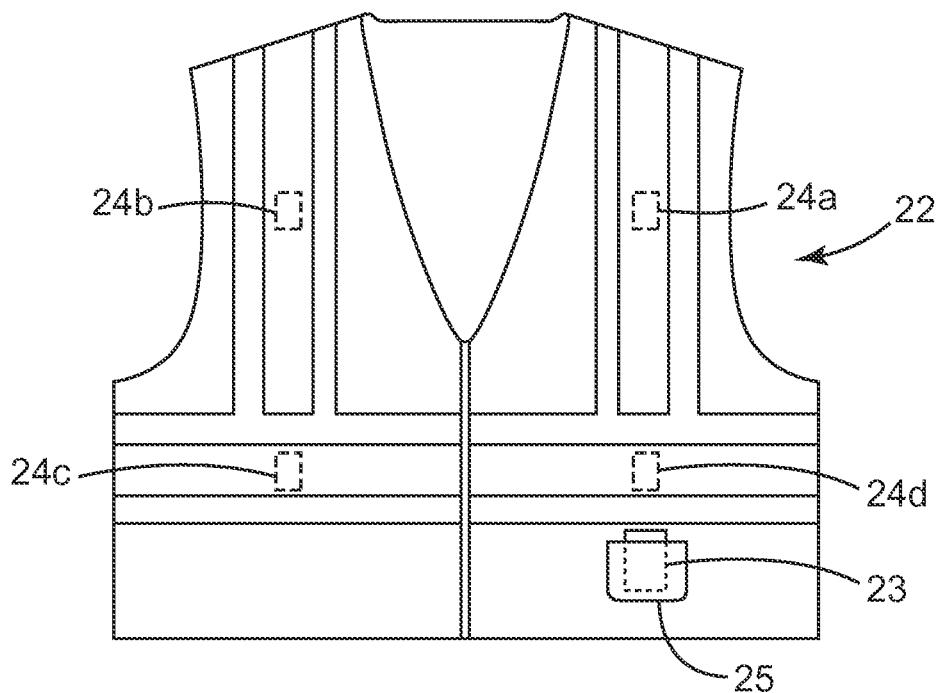
FIGS. 2a and 2b are examples of housings for a device for monitoring impairment indicators.
Figure 2B:
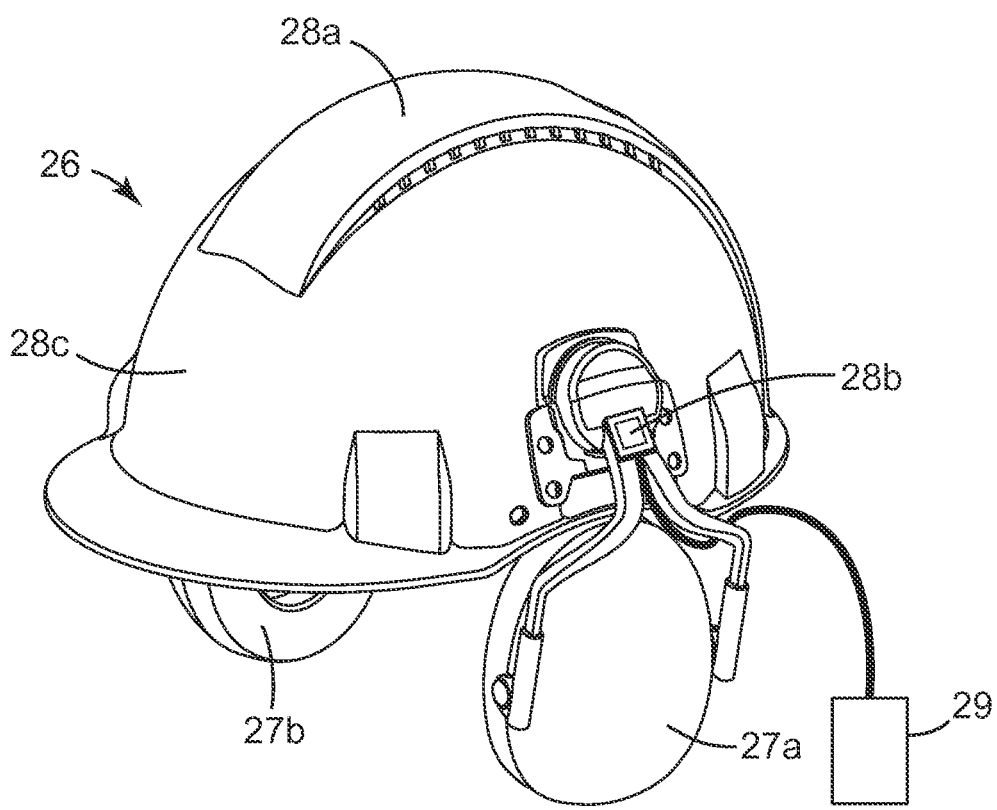

FIGS. 2a and 2b are examples of housings for a device for monitoring impairment indicators. FIG. 2a shows a high visibility safety vest 22. Vest 22 is a typical component of personal protective equipment (PPE) for many occupations and tasks, including construction, mining, road work, and in other fields and contexts. Vest 22 ensures that the wearer can be easily seen by, for example, other workers, oncoming vehicles and drivers of equipment. Vest 22 may also be a housing for a device for detecting impairment indicators. Movement sensors may be embedded at various locations in the vest, for example, at locations 24a, 24b, 24c, and 24d. The variety of locations allows for increased reliability of movement data. Vest 22 may be designed to include a pocket or other holding mechanism to carry other components of an impairment monitoring device. Pocket 23 provides an exemplary accessible enclosure for components such as the processor, communication unit, battery and other components that may be enclosed in a single unit 25. Unit 25 may communicate with movement sensors at locations 22a-22d through a wired connection embedded or enclosed in vest 22, or through a wireless connection.

FIG. 2b shows a hard hat 26 that also includes ear protection. Hard hat 26 is an important piece of PPE that may be worn for many occupations and tasks, including construction, mining, road work, along with other fields and contexts. Hard hat 26 includes hearing protection muffs 27a and 27b. In some instances, muffs 27a and 27b may include noise cancellation capabilities and/or a speaker or other communication-related components. Hard hat 26 may be a housing for an impairment monitoring device. For example, movement sensors may be located at various locations 28a, 28b, and 28c throughout hardhat 26 to allow for increased movement data reliability. Hard hat 26 may have a unit 29 including components such as a processor, communication unit, battery, and other components that may be enclosed in a single unit 29. Unit 29 may be in communication with movement sensors through a wired or wireless connection. In some instances, unit 29 is integrated into the structure of hard hat 26 and in other instances (as illustrated in FIG. 2b) it may be in a physically separate structure from hard hat 26, and connected to the movement sensors embedded in hard hat 26 by a wired or wireless connection.

Figure 3:
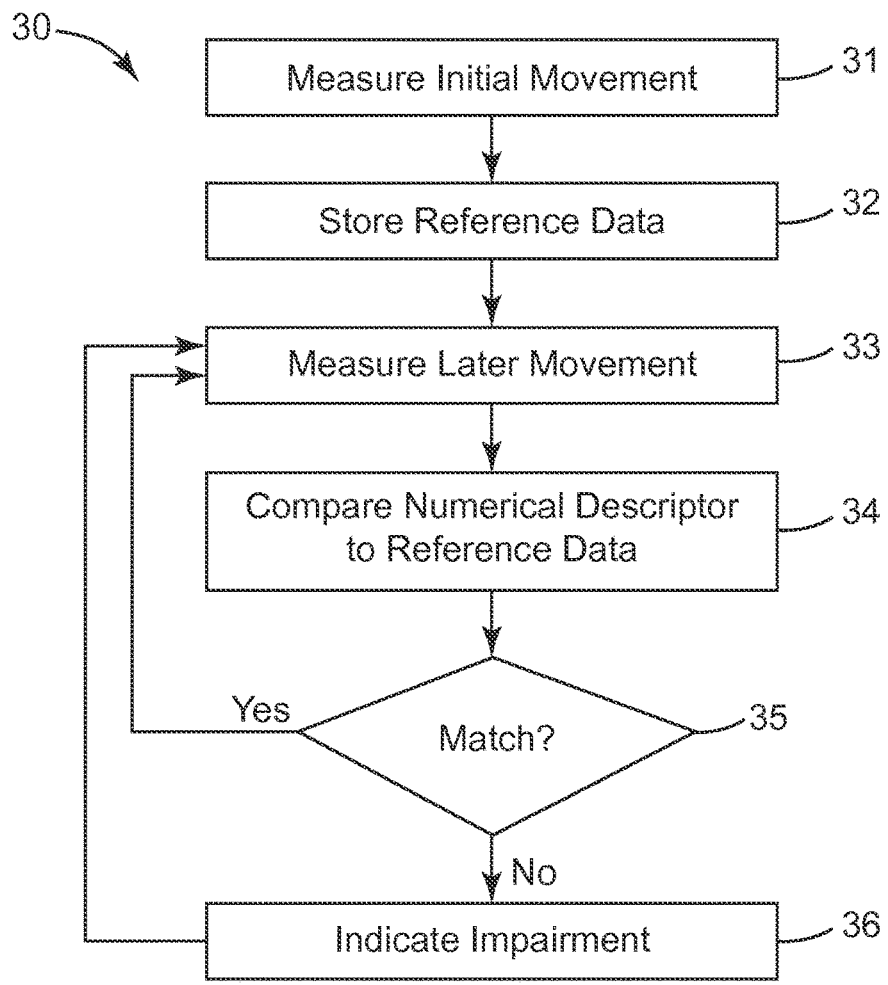
FIG. 3 is a flow chart representing a method of monitoring impairment indicators.

FIG. 3 is a flow chart representing a method of monitoring impairment indicators. The method includes, in step 31 measuring, with a movement sensor attached to a person, a first signal related to movement of the person during a first time window. The first signal may include a variety of information. For example, the first signal may be the output of a capacitive accelerometer measured as a scalar voltage. The first signal may also be the output of a piezoelectric accelerometer measured as a scalar current or voltage. The time window may be any given period of time over which to measure the first signal. As described above, the time window may be in the range of two seconds to ten seconds, and may be between those numbers, shorter or longer. In some instances, the movement sensor may measure the first signal over multiple time windows to increase the sample size which increases the accuracy of the measurement. In other instances, multiple sensors may each measure a signal related to movement of the person over the same time window. The plurality of data sets may increase reliability of measurement.

In some instances, the first time window occurs during a training activity performed by the person. A training activity may be completed through a series of prescribed motions while the device is placed into a special training mode. The training could be performed by an authorized trainer (e.g., a parole officer or a safety manager), and the trainer could show the person wearing the device a video instructing them on the types of movements to perform during the training period. After the training period is complete, the trainer returns the device to a normal monitoring mode.

In other instances, the movement of the person during the first time window occurs during their initial use of the impairment indicator device. In this case, the device begins detecting the movements of the person to capture the signals associated with the user defined movement. The device then may detect anomalies when they are compared to previously detected signals. In some instances, the movement of the person during the first time window is walking, and in other instances, the movement may be another designated movement.

In step 32, the processor stores at least one numerical descriptor derived from the first signal as reference data for the person. The numerical descriptor is a number computed based on the data sampled from a signal measured by the movement sensor. The numerical descriptor may be based on a single measured signal or on multiple measured signals. For example, when the movement sensor detects inertial movement along three axes, the numerical descriptor may be calculated based on the data associated with one axis, any combination of two axes, a computation involving each of the three axes or any combination thereof. The numerical descriptor may be determined for each data point related to the measured signal(s) or may be based on a lower sampling rate than the data from the measured signals. In some instances, two or more numerical descriptors may be associated with each time window.

The numerical descriptor may be stored as reference data, forming a baseline for the particular type of movement for the individual. For example, when the activity performed by the person during the first time window is walking, the numerical descriptor for their activity during at least the first time window is compared to future collected data to identify indication of impairment of the person at that future time.

In step 33, the movement sensor measures a second signal related to movement of the person during a second time window. The second time window may be chronologically adjacent with the first time window, or may be later in time. In some instances, the movement sensor may measure the second signal over multiple time windows to increase the sample size to provide a broader sample set for comparison to reference data. In other instances, multiple sensors may each measure a signal related to movement of the person over the same time window. The plurality of data sets may increase reliability of measurement.

In step 34, the processor compares at least one numerical descriptor derived from the second signal to the reference data as a factor to identify an impairment indicator. If there is alignment (within a tolerance) between the numerical descriptor and the reference data, the processor identifies normal behavior. The parameters of detection of an impairment indicator can be tuned based on the application. Further, a tolerance may be tighter where accurate identification of impairment is critical or where there is a higher cost of impairment is mis-identified. Alignment may be determined by a simple thresholding process and may also be determined by using a multi-dimensional classification algorithm, in which case multiple numerical descriptors would be required. In step 35, the processor determines if a match exists between the two signals within a tolerance. If there are sufficient differences between the reference data and second signal and a match does not occur as defined in the "no" path of step 35, then the processor identifies an impairment indicator as shown in step 36. An impairment indicator is indicative of at least one of mental impairment, visual impairment and physical impairment. These types of impairments may include specific impairments. For example, mental impairment includes at least distraction. Visual impairment includes at least prohibited substance abuse. And physical impairment includes at least physical injury and vestibular confusion.

If a match exists between the two signals as identified in the "yes" path of step 35 or no impairment indicator is identified as defined in step 36, the device continues to measure movement by returning to step 33. If an impairment indicator is detected, the device stores that result and in some instances, at least one of a local alarm and a remote alarm is triggered. The device then continues to measure movement as shown in step 33.

Figure 4:
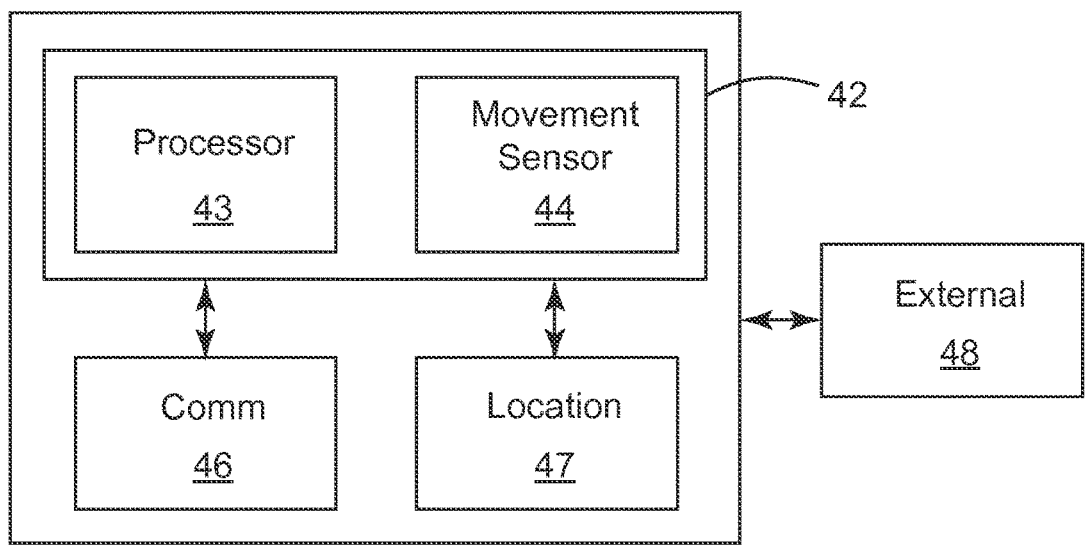
FIG. 4 is a block diagram of a device for monitoring impairment indicators.

FIG. 4 is a block diagram of a device 40 for monitoring impairment indicators. The device includes a processing unit 42 including both a processor 43 and a movement sensor 44. Processor 43 may be any type of processor or microprocessor commonly used to process information or to control a variety of other electronic components. Processor 43 interacts with movement sensor 44 to receive data from movement sensor 44, such as a signal related to the movement of the person wearing impairment monitoring device 40. Movement sensor 44 may be configured to measure such a signal during a time window as defined by processor 43.

Movement sensor 44 may be at least one of: an accelerometer, a gyroscope, a piezoelectric vibration sensor, a geographical positioning sensor and a magnetic switch. Movement sensor 44 may include more than one movement sensor. Movement sensor 44 measures a first signal related to movement of the person wearing impairment monitoring device 40 during a first time window. The processor 43 stores at least one numerical descriptor derived from the first signal with the activity label as reference data for the person. In some embodiments, the processor 43 may store the reference data with an assigned activity label, such as walking, running, or biking.

An exemplary time window may be in the range of 2 (two) seconds to 10 (ten) seconds and may contain a number of samples in the range of 8 (eight) to 1024 samples, as an example, not as a limitation. Movement sensor 44 may also be configured to operate in a very low power mode where sampling takes place occasionally over a longer time period, for example, once every five minutes, when the individual is sleeping or doing some other sedentary and longer-term activity. In general, data collection by the movement sensor 44 could range between 0.2 Hz and 50 Hz in frequency, but is not limited to previously defined range. The data collection frequency may be dependent upon the type of activity being detected. For example, faster moving activities, such as running, may require a higher sample rate (closer to 50 Hz) than slower moving activities such as sleeping. The size of a time window may also be related to data collection rate.

A time window should have enough samples for the data collected to store as reliable reference data.

Movement sensor 44 then measures a second signal related to movement of the person during a second time window and processor 43 compares at least one numerical descriptor derived from the second signal to the reference data to identify an impairment indicator. Comparison may include an algebraic sum or difference or other statistical variation such as mean, standard deviation, or variance. In an embodiment, the first signal (or reference data) may be a voltage represented numerically as 3.3 volts and the second signal may be recorded (also numerically) as a voltage of 1.3 volts. Processor 43 may compute the absolute difference between the first and second signal as 2.0 volts and determine whether the variation is above or below a threshold that indicates impairment and triggers an alarm. In a scenario requiring a tighter tolerance, the parameters and threshold values would be required to adapt accordingly. In some instances, the threshold may be tuned automatically based on acceptable error rate. In other instances, the threshold may be dynamically adjusted to compensate for other factors.

Movement sensor 44 may either be contained in the same physical unit as processor 43 or may be connected to processor 43 in a wired or wireless configuration. Device 40 may further include a location unit 47. The location unit 47 may be any device that provides an estimated geographical location for impairment monitoring device 40. Examples of a location unit 47 include the following technologies: GPS, Cellular Triangulation, WiFi triangulation and GNSS. In some configurations, processor 43 may be configured to estimate a location of the person using at least both of the signal from the movement sensor and data from the location unit. In some configurations, device 40 may use the location of the person as estimated by location unit 47 as a second factor to identify an impairment indicator.

Device 40 may also include a communications unit 46 to allow device 40 to communicate with external devices 48. For example, when an impairment indicator is detected, a local alarm or a remote alarm in external device 48 may be triggered.

While not shown in FIG. 4, impairment monitoring device 40 may further include an emergency notification component. Emergency notification component may be triggered manually, such as by a button or switch. When emergency notification component is triggered, communication unit 46 may transmit information to external device 48. External device 48 may be a central monitoring system, an emergency alert system, or other location. The information transmitted may include the location of device 40, the time the emergency notification is transmitted, and the reason that the emergency notification is transmitted.

Figure 5A:
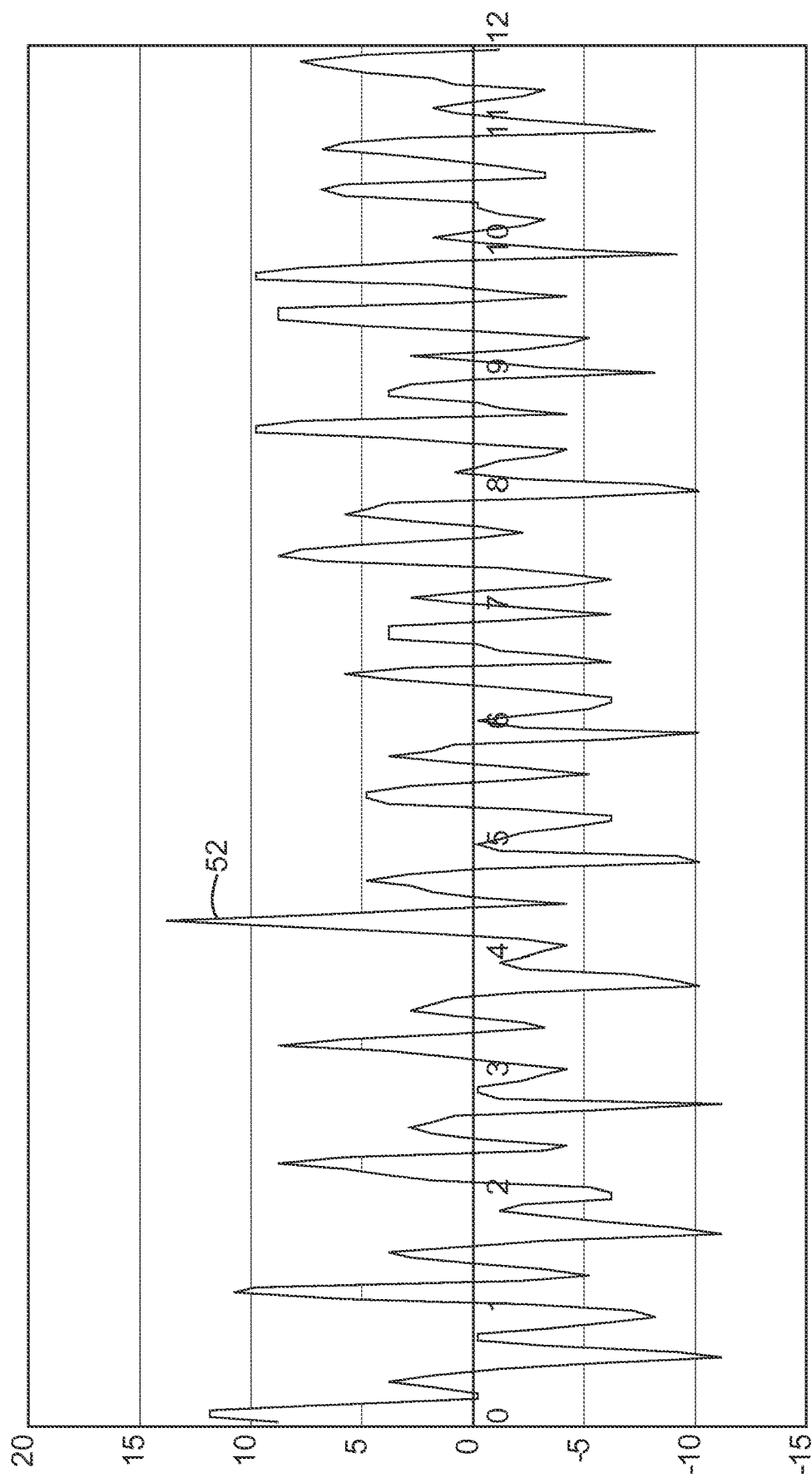
FIGS. 5a and 5b show exemplary data from a movement sensor over multiple time windows.
Figure 5B:
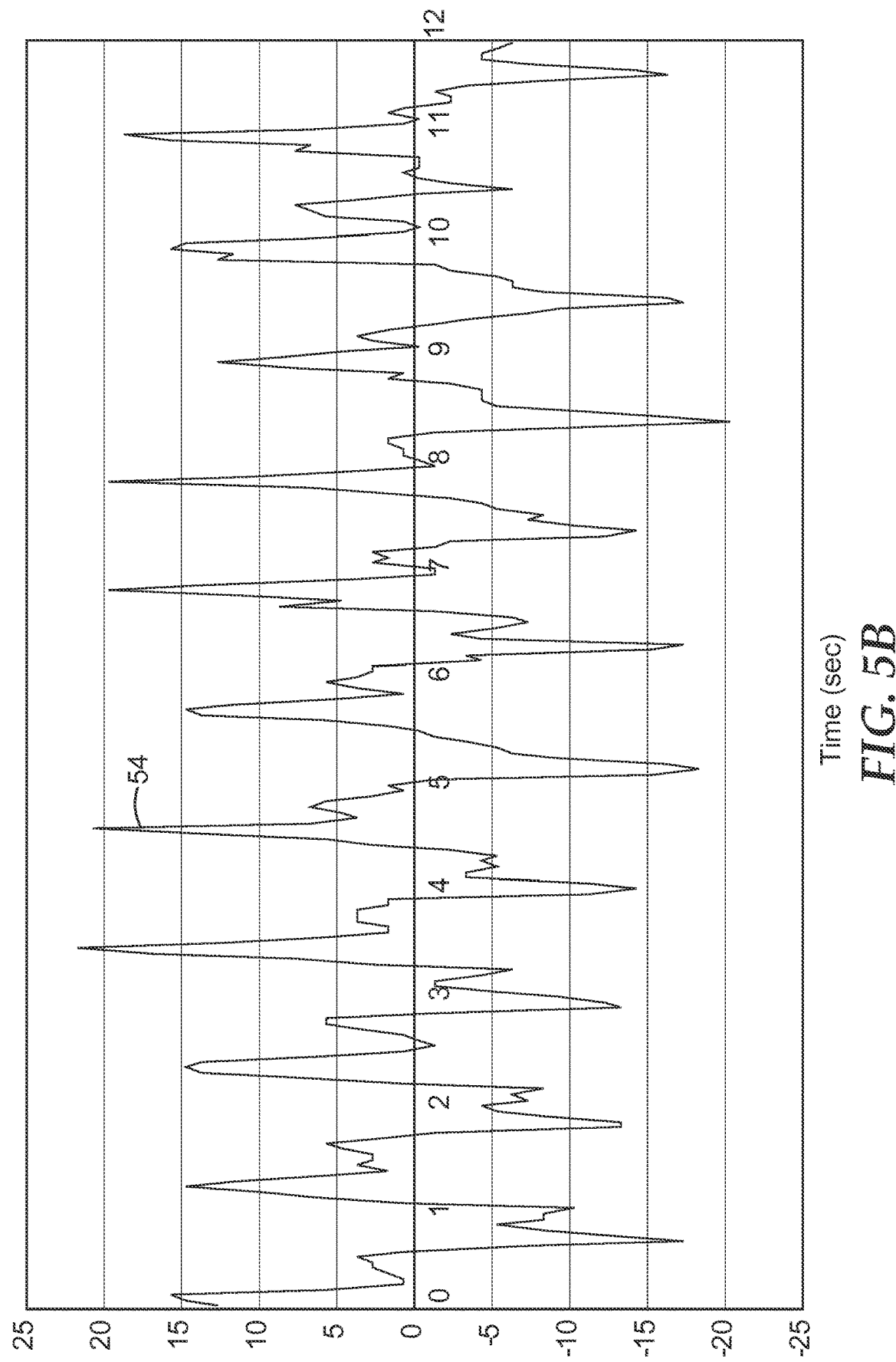

The signal from the movement sensor 44 is a digital representation (for example, a number between 0 and 1023) of an analog voltage output from the sensor describing the motion FIGS. 5*a* and 5*b* show exemplary data from a movement sensor over multiple time windows. FIG. 5*a* shows a first signal 52 related to movement of a person over several time windows. The signal is shown in a graph where the vertical axis represents time in seconds and the horizontal axis represents the scalar value related to the level of movement detected by the movement sensor. Signal 52 is collected over twelve 1-second time windows, where each time window contains 20 samples. The sampling rate is 20 Hz. The first signal is taken while the person wearing the device is walking and is stored as reference data for the person.

FIG. 5*b* shows a second signal 54 related to movement of the person measured over several time windows. The signal is shown in a graph where the vertical axis represents time in seconds and the horizontal axis represents the scalar value related to the level of movement detected by the movement sensor. Signal 54 is collected over twelve 1-second time windows, where each time window contains 20 samples. Numerical descriptors derived from the second time window were compared to the reference data derived from signal 52 and the resulting differences indicated the presence of an impairment during the time period shown in FIG. 5*b*.

The techniques of this disclosure may be implemented in a wide variety of computer devices, such as servers, laptop computers, desktop computers, notebook computers, tablet computers, hand-held computers, smart phones, and the like. Any components, modules or units have been described to emphasize functional aspects and do not necessarily require realization by different hardware units. The techniques described herein may also be implemented in hardware, software, firmware, or any combination thereof. Any features described as modules, units or components may be implemented together in an integrated logic device or separately as discrete but interoperable logic devices. In some cases, various features may be implemented as an integrated circuit device, such as an integrated circuit chip or chipset. Additionally, although a number of distinct modules have been described throughout this description, many of which perform unique functions, all the functions of all of the modules may be combined into a single module, or even split into further additional modules. The modules described herein are only exemplary and have been described as such for better ease of understanding.

If implemented in software, the techniques may be realized at least in part by a computer-readable medium comprising instructions that, when executed in a processor, performs one or more of the methods described above. The computer-readable medium may comprise a tangible computer-readable storage medium and may form part of a computer program product, which may include packaging materials. The computer-readable storage medium may comprise random access memory (RAM) such as synchronous dynamic random access memory (SDRAM), read-only memory (ROM), non-volatile random access memory (NVRAM), electrically erasable programmable read-only memory (EEPROM), FLASH memory, magnetic or optical data storage media, and the like. The computer-readable storage medium may also comprise a non-volatile storage device, such as a hard-disk, magnetic tape, a compact disk (CD), digital versatile disk (DVD), Blu-ray disk, holographic data storage media, or other non-volatile storage device.

The term "processor," as used herein may refer to any of the foregoing structure or any other structure suitable for implementation of the techniques described herein. In addition, in some aspects, the functionality described herein may be provided within dedicated software modules or hardware modules configured for performing the techniques of this disclosure. Even if implemented in software, the techniques may use hardware such as a processor to execute the software, and a memory to store the software. In any such cases, the computers described herein may define a specific machine that is capable of executing the specific functions described herein. Also, the techniques could be fully implemented in one or more circuits or logic elements, which could also be considered a processor.

Variations on the disclosure described above will be apparent to one of skill in the art upon reading the present disclosure, and are intended to be included within the scope of the present disclosure. A wide range of activities may be detected in addition to those discussed explicitly herein, and are within the scope of the present disclosure. Further, a variety of analysis methods may be used consistent with the disclosed analysis steps and processes.

What is claimed is:

1. A computing device comprising:
a physical housing configured to be worn by a worker; wherein the physical housing is a safety vest that is a component of personal protective equipment (PPE);
multiple movement sensors enclosed within the physical housing in multiple locations, located at a distance from each other and from other components within the physical housing, wherein the other components communicate with the movement sensors; wherein the physical housing includes a pocket that encloses the other components and wherein the multiple movement sensors are located on opposite sides of the physical housing;
wherein the other components include:
at least one computer processor enclosed within the physical housing; and
at least one memory enclosed within the physical housing;
wherein the at least one memory comprises instructions that, when executed by the at least one computer processor, cause the at least one computer processor to:
place the device in a training mode;
in training mode based on a first set of one or more signals that correspond to movement of the worker performing a series of prescribed motions of a training activity, the first set of one or more signals measured by the movement sensors during a first time window, generate a first numerical descriptor for the first time window that corresponds to the worker not being under the influence of a prohibited substance during the first time window;
after generating the first numerical descriptor return the device to a normal monitoring mode;
in normal mode based on a second set of one or more signals that correspond to movement of the worker in a work context measured by the movement sensors during a second time window, generate a second numerical descriptor for the second time window;
determine a variation between the first numerical descriptor and the second numerical descriptor;
determine the variation between the first numerical descriptor and the second numerical descriptor satisfies a threshold;
determine an impairment indicator indicative of a prohibited substance abuse based on determining the variation between the first numerical descriptor and the second numerical descriptor satisfies the threshold;
trigger a remote alarm at an external device based at least in part on the impairment indicator.

2. The computing device of claim 1, wherein the memory comprises instructions that, when executed by the at least one computer processor, cause the at least one computer processor to generate, based at least in part on the impairment indicator, data that indicates a requirement for the worker to perform a testing activity.

3. The computing device of claim 1, wherein the memory comprises instructions that, when executed by the at least one computer processor, cause the at least one computer processor to:
in response to receiving from each respective sensor of the multiple movement sensors, a respective set of sensor data based on one or more signals generated by the respective sensor during a time window, generate the second numerical descriptor for the second time window.

4. The computing device of claim 1, wherein the memory comprises instructions that, when executed by the at least one computer processor, cause the at least one computer processor to:
generate a plurality of numerical descriptors for the time window that includes the second numerical descriptor for the second time window.

5. The computing device of claim 1, wherein the memory comprises instructions that, when executed by the at least one computer processor, cause the at least one computer processor to:
trigger a local alarm based at least in part on the impairment indicator.

6. The computing device of claim 1, wherein the memory comprises instructions that, when executed by the at least one computer processor, cause the at least one computer processor to:
apply a multi-dimensional classification algorithm to the first and second numerical descriptors.

7. The computing device of claim 1, wherein a sampling rate to generate the second numerical descriptor is less than a sampling rate of the movement sensors to generate the second set of one or more signals.

8. The computing device of claim 1, wherein the first set of one or more signals that correspond to movement of the worker during the first time window are performed by the worker during an initial use of the computing device.

9. The computing device of claim 8, wherein the initial use of the computing device is a walking movement.

10. The computing device of claim 1, wherein the computing device is configured with an article of PPE.

11. The computing device of claim 10, wherein the article of PPE comprises a hard hat.

12. The computing device of claim 1, wherein the work context corresponds to at least one of a working location, occupation, or task.

13. The computing device of claim 1, wherein a sampling rate of the second set of one or more signals is dependent on the type of activity being detected.

14. The computing device of claim 13, wherein a size of the second time window is related to the sampling rate.

15. The computing device of claim 1, wherein the first numerical descriptor and second numerical descriptor represent voltage of a sensor.

* * * * *